United States Patent
Lehmann et al.

(10) Patent No.: US 7,132,462 B2
(45) Date of Patent: *Nov. 7, 2006

(54) TWO-COMPONENT DENTAL MATERIALS HAVING A LOW SETTING TEMPERATURE

(75) Inventors: Thomas Lehmann, Burghausen (DE); Reinhold Hecht, Inning-Buch (DE)

(73) Assignee: 3M ESPE AG, Seefeld (DE)

( * ) Notice: Subject to any disclaimer, the term of this patent is extended or adjusted under 35 U.S.C. 154(b) by 269 days.

This patent is subject to a terminal disclaimer.

(21) Appl. No.: 10/257,011

(22) PCT Filed: Apr. 4, 2001

(86) PCT No.: PCT/EP01/03834

§ 371 (c)(1), (2), (4) Date: Feb. 12, 2003

(87) PCT Pub. No.: WO01/76536

PCT Pub. Date: Oct. 18, 2001

(65) Prior Publication Data

US 2003/0158288 A1    Aug. 21, 2003

(30) Foreign Application Priority Data

Apr. 7, 2000  (DE) ................. 100 17 188

(51) Int. Cl.
- A61C 5/00 (2006.01)
- A61K 6/10 (2006.01)
- A61K 6/083 (2006.01)
- A61F 2/00 (2006.01)
- C01F 4/28 (2006.01)

(52) U.S. Cl. .............. 523/109; 523/113; 523/115; 523/120; 526/217; 526/220; 526/227; 433/226; 433/228.1

(58) Field of Classification Search ......... 523/109, 523/113, 115, 120; 526/217, 220, 227; 433/226, 433/228.1

See application file for complete search history.

(56) References Cited

U.S. PATENT DOCUMENTS 6,610,759 B1 *  8/2003  Chappelow et al. .......... 522/25

6,852,775 B1 *  2/2005  Soglowek et al. .......... 523/109

FOREIGN PATENT DOCUMENTS

| DE | 955633 | 1/1957 |
| DE | 975072 | 8/1961 |
| DE | 1495520 | 4/1969 |
| DE | 35 14 283 A1 | 10/1986 |
| DE | 4219700 | 12/1992 |
| DE | 691 23 811 T2 | 4/1997 |
| DE | 19914975 | 10/2000 |
| DE | 199 28 238 A1 | 12/2000 |
| EP | 0235826 | 1/1990 |
| EP | 0374824 | 6/1990 |
| WO | WO 00/78271 A1 | 12/2000 |

OTHER PUBLICATIONS

Office Action from corresponding German patent application number 100 17 188.5-42 dated Oct. 26, 2004 with English language translation.

Office Action from corresponding German patent application number 100 17 188.5-42 dated Jun. 21, 2002.

* cited by examiner

Primary Examiner—Tae H. Yoon
(74) Attorney, Agent, or Firm—Crowell & Moring LLP

(57) ABSTRACT

The invention relates to polymerizable materials comprising two components, where component I comprises: (a) from 0.1 to 20% by weight of at least one vinyl ether, (b) from 10 to 89.9% by weight of at least one ethylenically unsaturated monomer which is not a vinyl ether, (c) from 0.001 to 5% by weight of at least one accelerator, (d) from 9.999 to 89.899% by weight of fillers, thixotropy assistants, retardants and other auxiliaries, and component II comprises: (e) from 0.1 to 20% by weight of at least one barbituric acid derivative and/or at least one malonylsulfamide which is able to initiate the free-radical polymerization, and (f) from 0 to 89.9% by weight of fillers, thixotropy assistants, retardants and other auxiliaries, (g) from 10 to 80% by weight of conventional plasticizers, and to the use thereof.

11 Claims, No Drawings

TWO-COMPONENT DENTAL MATERIALS HAVING A LOW SETTING TEMPERATURE

The present invention relates to two-component, free-radical-polymerizable dental materials which exhibit a low temperature increase during setting and have good final mechanical hardness.

Dental materials of this type usually consist of a monomer mixture, an initiator system, fillers, additives and optionally plasticizers.

The monomers used in polymerizable dental materials are, in particular, unsaturated compounds, such as acrylic and methacrylic esters.

On use of these dental materials, the monomers are mixed with a suitable initiator system, forming a paste-form material, which cures by free-radical polymerization.

The free-radical-polymerization initiators employed are various redox initiator systems.

An initiator system which has been known for some time consists of an amine component and a peroxide component, as described in German Patent 975 072. The polymerization here is initiated by the peroxide compound. As polymerization accelerator, use is made, for example, of a tertiary aromatic amine.

A further system of this type is also described by Albert Gross in "Quintessenz der Zahntechnik" [Quintessence of Dental Technology], 1977, 7, paper No. 293. Therein, secondary or tertiary amines accelerate the decomposition of the peroxide component, which initiates the polymerization of the monomers. The amine component here is usually incorporated into a paste, the so-called base paste. This base paste also comprises the monomers intended for polymerization. The peroxide component is incorporated into a further paste, the so-called catalyst paste. The spatial separation of the two initiator components is necessary in order to prevent premature curing of the monomers.

German Patent DE 955 633 likewise describes a similar initiator system for the polymerization of unsaturated hydrocarbons which comprises heavy metals and an amine component and a sulfone component.

EP-B-0 374 824 likewise mentions an initiator system comprising an organic peroxide compound and a tertiary aromatic amine as activator (accelerator).

The disadvantage of dental materials comprising this initiator system is that the aromatic amines which are suitable for a favorable setting phase tend toward discoloration. However, these yellow-brown color changes are unacceptable in the dental area. In addition, tertiary aromatic amines can only be employed to a limited extent owing to their health risk. A further problem is the increase in temperature during polymerization of the systems owing to the exothermic processes. Excessive heat evolution can result in pulp damage in the patient.

More favorable temperature evolution and also better color stability are exhibited by the initiator systems described, for example, in DT-C-14 95 520. The composition therefrom polymerizes with a relatively small temperature increase in a short time and without supply of external energy. The systems described comprise barbituric acid derivatives or malonylsulfamides, organic peroxides, ionogenically bound halogen and/or a heavy-metal compound.

EP-B-0 374 824 also describes an initiator system of this type comprising barbituric acid derivative, peroxide, heavy-metal compound and ionogenic halogen. In these initiator systems, barbituric acid derivatives or malonylsulfamides and peroxides cannot be stored together. Furthermore, the two initiator system constituents mentioned must be stored separately from the monomers. Storage in three spatially separate pastes is thus necessary for the provision of polymerizable dental materials comprising monomers, barbituric acid derivatives or malonylsulfamides, organic peroxides, ionogenically bound halogen and/or a heavy-metal compound.

This results in relatively complex handling of the systems. Thus, three-component systems are not suitable for automatic mixing. These conventional dental materials comprising three components therefore have to be mixed by hand, during which air is incorporated and the individual components cannot be dispensed precisely. The incorporation of air should be avoided in particular because air bubbles cause the formation of flaws in the cured material. This results in an increase in fracture sensitivity and poor surface quality. Different dispensed amounts result in modified setting times, impaired mechanical properties and inaccurate coloration. Furthermore, hand mixing takes longer than automatic mixing.

Furthermore, DT-C-14 955 20 describes methacrylate polymerizations in solvents which comprise barbituric acid derivatives or malonylsulfamides, ionogenically bound halogen and/or a heavy-metal compound and cure with oxygen instead of with organic peroxides.

If, however, it is attempted to store these systems in cartridges with no solvent, curing does take place after mixing, but the mechanical values of the cured material are lower than in the case of addition of peroxides, which in turn produce a higher setting temperature and are toxicologically unfavorable.

The object of this invention is to provide a dental material which cures on the basis of an initiator system comprising barbituric acid derivative and/or malonylsulfamide, optionally an ionogenically bound halogen, a heavy-metal compound and oxygen, and avoids the disadvantages of the prior art.

Surprisingly, it has been found that the addition of vinyl ethers to base pastes based on ethylenically unsaturated monomers which are not vinyl ethers enables higher mechanical values to be achieved and keeps the setting temperature low.

The materials according to the invention consist of two components, where component I comprises:

(a) from 0.1 to 20% by weight, preferably from 0.5 to 18% by weight and particularly preferably from 1 to 13% by weight, of at least one vinyl ether, (b) from 10 to 89.9% by weight, preferably from 24.5 to 89% by weight and particularly preferably from 30 to 85% by weight, of at least one ethylenically unsaturated monomer which is not a vinyl ether, (c) from 0.001 to 5% by weight, preferably from 0.002 to 4% by weight and particularly preferably from 0.005 to 3% by weight, of at least one accelerator, (d) from 9.999 to 89.899% by weight, preferably from 15 to 85% by weight and particularly preferably from 20 to 70% by weight, of fillers, thixotropy assistants, retardants and other auxiliaries, and component II comprises (e) from 0.1 to 20% by weight, preferably from 1 to 18% by weight and particularly preferably from 3 to 13% by weight, of at least one barbituric acid derivative and/or at least one malonylsulfamide which is able to initiate the free-radical polymerization, and (f) from 0 to 79.9% by weight, preferably from 1 to 69% by weight and particularly preferably from 5 to 60% by weight, of fillers, thixotropy assistants, retardants and other auxiliaries, (g) from 20 to 80% by weight, preferably from 30 to 75% by weight and particularly preferably from 35 to 70% by weight, of conventional plasticizers.

Hereinafter, component I is also referred to as the base paste and component II as the catalyst paste.

The term constituent (a) is taken to mean mono-, di- or multifunctional vinyl ethers, such as $C_3$- to $C_{40}$-alkyl vinyl ethers, preferably $C_4$- to $C_{30}$-alkyl vinyl ethers, $C_8$- to $C_{40}$-aryl vinyl ethers, preferably $C_8$- to $C_3O$-aryl vinyl ethers, aryl alkylvinyl ethers and cycloaliphatic vinyl ethers. Likewise possible are oligomeric or polymeric vinyl ethers, such as polyether vinyl ethers, polyacrylate vinyl ethers, polyester vinyl ethers, polycarbonate vinyl ethers, polyimide vinyl ethers, polyamide vinyl ethers, phosphazene vinyl ethers, siloxane vinyl ethers and polyurethane vinyl ethers. It is advantageous for the molecular weight of the oligomeric or polymeric vinyl ethers to be less than 15,000 g/mol, preferably less than 10,000 g/mol. It is furthermore favorable for the preparation of the dental materials for the vinyl ethers to be in the form of a liquid at room temperature. The vinyl ethers may of course also contain further functional groups, such as hydroxyl groups, epoxide groups and (meth)acryloxy groups. Examples thereof are dimethanolcyclohexyl monovinyl ether, triethylene glycol monovinyl ether mono-(meth)acrylate and cyclohexyl 3,4-epoxy-1-methylvinyl ether.

Particularly suitable are ethylene glycol divinyl ether, diethylene glycol divinyl ether, 7,7,9-trimethyl-4,13-dioxo-3,14-dioxa-5,12-diazahexadecane-1,16-dioxydivinyl ether, triethylene glycol divinyl ether (BASF, Ludwigshafen), isopropyl vinyl ether, tetraethylene glycol divinyl ether, tripropylene glycol divinyl ether, 1,4-dimethanol cyclohexyl divinyl ether (ISP, Guildford), divinyl ethers of propanediol, butanediol, hexanediol, octanediol, nonanediol, decanediol and eicosanediol, octyl vinyl ether, octadecyl vinyl ether, glycerol trivinyl ether, pentaerythritol tetravinyl ether, bisphenol A divinyl ether, divinyl ethers of bishydroxymethyltricyclo(5.2.1.0$^{2,6}$)decane and divinyl ethers of ethoxylated and/or propoxylated bisphenol A or bisphenol C.

Also particularly suitable are the vinyl ethers from the above group having a viscosity of less than 1 Pas at 23° C. and in particular less than 0.5 Pas at 23° C., since they have the additional advantage of lowering the viscosity of the dental materials, simplifying application from cartridges and automatic mixing.

Difunctional vinyl ethers are in general particularly suitable.

Ethylenically unsaturated monomers of component (b) are monofunctional or bi- or polyfunctional ethylenically unsaturated monomers, with the exception of vinyl ethers.

For the purposes of the present invention, the term ethylenically unsaturated monomers is also taken to mean polymerizable compounds which have an oligomeric or polymeric basic structure and carry at least one ethylenically unsaturated group. This ethylenically unsaturated group can be, for example, in the form of an acrylate and/or methacrylate group which is covalently bonded to the basic structure. The polymeric basic structure can be, for example, a polyethylene oxide, a polyester, a polyvinyl ester derivative, a polyurethane, a polycarbonate, a polyalcohol, a polystyrene or a polymerized ethylenically unsaturated compound. The molecular weight of these compounds should be less than 25,000 g/mol, in particular less than 15,000 g/mol.

Preferred ethylenically unsaturated monomers are methacrylate and acrylate monomers, such as methyl (meth)acrylate, n- or i-propyl (meth)acrylate, n-, i- or tert-butyl (meth)acrylate and 2-hydroxy(meth)acrylate, 2-(meth)acryloxytetrahydrofuran, 2-(((alkylamino)carbonyl)oxy)ethyl (meth)acrylates, di(meth)acrylates of propanediol, butanediol, hexanediol, octanediol, nonanediol, decanediol and eicosanediol, tetrahydrofurfuryl (meth)acrylate, di(meth)acrylates of ethylene glycol, of polyethylene glycols and of polypropylene glycols, di(meth)acrylates of ethoxylated bisphenol A, for example 2,2'-bis(4-(meth)acryloxytetraethoxyphenyl)propanes, urethane (meth)acrylates and (meth)acrylamides.

The monomers used can furthermore be esters of α-cyanoacrylic acid, crotonic acid, cinnamic acid and sorbic acid.

It is also possible to use the methacrylic esters mentioned in EP-A-0 235 826, such as bis(3[4]-methacryl-oxymethyl-8(9)-tricyclo[5.2.1.0$^{2,6}$]decylmethyl triglycolate.

Particularly suitable are 2,2-bis-4(3-methacryloxy-2-hydroxypropoxy)phenylpropane (bis-GMA), 2,2-bis-4(3-methacryloxypropoxy)phenylpropane, triethylene glycol dimethacrylate (TEGDMA), 7,7,9-trimethyl-4,13-dioxo-3,14-dioxa-5,12-diazahexadecane-1,16-dioxy dimethacrylate (UDMA), urethane (meth)acrylates and di(meth)acrylates of bishydroxymethyltricyclo-(5.2.1.0$^{2,6}$)decane.

These ethylenically unsaturated monomers can be employed in the dental materials according to the invention either alone or in combination with further ethylenically unsaturated monomers.

The use of more than about 10% by weight of urethane (meth)acrylates as monomers in constituent (b) has proven advantageous for this initiator system, particularly if they make up more than 50% by weight of (b) and in particular if (b) consists of more than 80% by weight of urethane (meth)acrylates. It is of course also possible for (b) to consist of 100% by weight of one or more urethane (meth)acrylates.

The urethane methacrylates can be, for example, low-molecular-weight compounds, such as 7,7,9-trimethyl-4,13-dioxo-3,14-dioxa-5,12-diazahexadecane-1,16-dioxy dimethacrylate and/or oligomeric or polymeric compounds, such as polyester urethane (meth)acrylates, polyether urethane (meth)acrylates, polycarbonate urethane (meth)acrylates and poly(meth)acrylate urethane (meth)acrylates. The molecular weight of these compounds is preferably less than 20,000 g/mol, particularly less than 15,000 g/mol and in particular less than 10,000 g/mol.

Suitable accelerators in accordance with constituent (c) are heavy-metal compounds, in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

It is also possible for ionogenically bound halogens or pseudohalogens, for example $Cl^-$-containing compounds, preferably in the form of soluble salts, in particular organic ammonium chlorides or hydrochlorides, to be added as additional accelerators. For example, it is possible to use dibutylamine hydrochloride, tributylamine hydrochloride, tetrabutylammonium chloride, triethylamine hydrochloride, (β-phenylethyl)dibutylammonium chloride and polyethyleneimine hydrochloride.

Furthermore, the polymerizable dental material according to the invention can comprise, as constituents (d) and (f), conventional fillers for dental materials, such as glass and quartz powders, silica gels, pyrogenic, highly disperse silicic acids, low-solubility fluorides and mixtures of these components. These fillers may be X-ray-opaque due to suitable additives, such as barium- and/or strontium-containing glasses. Examples of suitable thixotropy agents are pyrogenic, highly disperse silicic acids. Further assistants are, for example, dyes, pigments, flow improvers, polymeric thickeners or stabilizers. In order to increase the flexibility of the dental material, it is also possible to add soluble organic polymers, such as, for example, polyvinyl acetate, and copolymers thereof.

Christobalite, calcium silicate, zirconium silicate, montmorillonite, such as bentonites, zeolites, including molecular sieves, such as sodium aluminum silicate, metal oxide powders, such as aluminum oxides or zinc oxides or mixed oxides thereof, barium sulfate, yttrium fluoride, calcium carbonate, gypsum and polymer powders, are also suitable as fillers for the dental material according to the invention.

The said fillers can also be rendered hydrophobic by, for example, treatment with organosilanes or organosiloxanes or by etherification of hydroxyl groups to give alkoxy groups. The fillers preferably have a particle size of less than 0.100 mm, in particular less than 0.050 mm and very particularly less than 0.025 mm. For particularly smooth surfaces and good polishability, it is advantageous to employ fillers smaller than 0.005 mm.

Suitable retardants are the compounds described in EP-B-0 374 824.

The barbituric acid derivatives and/or malonylsulfamides of component (e) all carry at least one acidic proton. In the case of the barbituric acid derivatives, this is located in position 5 of the six-membered ring. It is possible to employ, for example, alkyl-, aryl- and/or cycloalkyl-substituted barbituric acid derivatives and/or malonylsulfamides. For example, the following compounds can be employed: 1,3,5-trimethylbarbituric acid, 1,3,5-triethylbarbituric acid, 1,3-dimethyl-5-ethylbarbituric acid, 1,5-dimethylbarbituric acid, 1-methyl-5-ethylbarbituric acid, 1-methyl-5-propylbarbituric acid, 5-ethylbarbituric acid, 5-propylbarbituric acid, 5-butylbarbituric acid, 1-benzyl-5-phenylbarbituric acid, 1-cyclohexyl-5-ethylbarbituric acid and the thiobarbituric acids mentioned in DE-A-42 19 700.

Also highly suitable are the barbituric acids and barbituric acid derivatives described in DT-C-14 95 520 and the malonylsulfamides mentioned in EP-A-0 059 451. Preferred malonylsulfamides are 2,6-dimethyl-4-isobutylmalonylsulfamide, 2,6-diisobutyl-4-propylmalonylsulfamide, 2,6-dibutyl-4-propylmalonylsulfamide, 2,6-dimethyl-4-ethylmalonylsulfamide, and 2,6-dioctyl-4-isobutylmalonylsulfamide.

As constituent (g), conventional plasticizers may be present. These are, for example, polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate and silicone oils.

The mixing ratio of base paste to catalyst paste is preferably in the range from 1:1 to 50:1, particularly from 2:1 to 20:1 and in particular from 4:1 to 10:1.

The dental materials according to the invention are particularly suitable as filling materials, core buildup materials, dental cements, temporary crown and bridge materials, materials in dental technology, model material or for the production of inlays, onlays and veneers.

The invention also covers containers containing the two components of the dental materials, for example cartridges from the Mixpack company, Rotkreuz, tubes from the ESPE company, Seefeld, and other cartridges, bags, tubes and mixers.

EXAMPLES

In each case, 10 g of catalyst paste and 100 g of base paste are compounded under reduced pressure from the constituents listed in Table 1 and Table 2. These pastes are introduced into 10:1 cartridges from the Mixpack company, Rotkreuz. For use, they are pressed through a static mixing device by means of a disperser and mixed in the process, so that curing commences within a few minutes.

TABLE 1

| Constituent | Raw material | % by weight |
|---|---|---|
| Catalyst 1 with peroxide | | |
| (f) | fluoroaluminosilicate glass powder (Ø < 12 μm) | 36 |
| (e) | 1-benzyl-5-phenylbarbituric acid | 10 |
| Peroxide | 3,5,5-trimethylhexanoic acid tertiary-butyl perester (TBPIN) | 4 |
| (g) | 2,2-bis-4-(2-hydroxyethoxy-phenyl)propane bisacetate | 50 |
| Catalyst 2 without peroxide | | |
| (f) | fluoroaluminosilicate glass powder (Ø < 12 μm) | 34 |
| (e) | 1-benzyl-5-phenylbarbituric acid | 10 |
| (g) | 2,2-bis-4-(2-hydroxyethoxy-phenyl)propane bisacetate | 56 |

TABLE 2

| Constituent | Raw material | % by weight |
|---|---|---|
| Base 1 without vinyl ether | | |
| (d) | fluoroaluminosilicate glass powder (Ø < 12 μm) with methacryloxypropyl-trimethoxysilane | 25 silanized |
| (d) | microfine silicic acid silanized (HDKH 2000, Wacker) | 7 |
| (c) | bis(1-phenylpentane-1,3-dionato)copper(II) | 0.008 |
| (c) | (β-phenylethyl)dibutylammonium chloride | 0.352 |
| (b) | UDMA | 60.84 |
| (b) | triethylene glycol dimethacrylic acid ester | 6.8 |
| Base 2 with vinyl ether (according to the invention) | | |
| (d) | fluoroaluminosilicate glass powder (Ø < 12 μm) with methacryloxypropyl-trimethoxysilane | 25 silanized |
| (d) | microfine silicic acid silanized (KDKH 2000, Wacker) | 7 |
| (c) | bis(1-phenylpentane-1,3-dionato)copper(II) | 0.008 |
| (c) | (β-phenylethyl)dibutylammonium chloride | 0.352 |
| (b) | UDMA | 60.84 |
| (a) | 1,4-dimethanol cyclohexyl divinyl ether | 6.8 |

Mechanical Values and Setting Times:

TABLE 3

| Measurement value | Comparative example | Comparative example | Example according to the invention |
|---|---|---|---|
| | Base 1/ Catalyst 1 | Base 1/ Catalyst 2 | Base 2/ Catalyst 2 |
| Start of setting [sec] | 35 | 75 | 40 |
| End of setting [sec] | 80 | 165 | 95 |
| Maximum setting temperature [° C.] | 73 | 49 | 51 |
| Modulus of elasticity in bending [MPa] | 1570 | 990 | 1620 |

Setting times: Curometer (Wallace-Shawbury, England);

Modulus of elasticity: 3-point flexural test with 4 mm*6 mm*25 mm flexural test specimens, supported at a separation of 20 mm, loading in the center (Zwick, Germany);

Temperature measurement: for the temperature measurement, a Delrin cylinder with internal dimensions of diameter 10 mm and height 10 mm was filled with the mixed material, and the maximum setting temperature in the material was measured.

It is evident from Table 3 how high mechanical values can be achieved at low setting temperature with base 2 according to the invention, which comprises vinyl ether, and catalyst 2 according to the invention without peroxide.

The invention claimed is:

1. A polymerizable material, comprising:
   component I, which comprises
   a) about 0.1 to about 20% by weight of at least one vinyl ether,
   wherein said vinyl ether is selected from the group consisting of polyether vinyl ether, polyacrylate vinyl ether, polyester vinyl ether, polycarbonate vinyl ether, polyimide vinyl ether, polyamide vinyl ether, polyphosphazene vinyl ether, siloxane vinyl ether, and polyurethane vinyl ether
   b) about 10 to about 89.9% by weight of at least one ethylenically unsaturated monomer that is not a vinyl ether,
   c) about 0.001 to about 5% by weight of at least one accelerator, and
   d) about 9.999 to about 89.899% by weight of fillers, thixotropy assistants, and retardants; and
   component II, which comprises
   e) about 0.1 to about 20% by weight of at least one barbituric acid derivative or at least one malonylsulfamide to initiate the free-radical polymerization,
   f) about 0 to about 89.9% by weight of fillers, thixotropy assistants, and retardants, and
   g) about 10 to about 80% by weight of plasticizers.

2. The polymerizable material of claim 1, wherein said at least one vinyl ether includes at least one second vinyl ether selected from the group consisting of alkyl vinyl ethers, aryl vinyl ethers, aryl alkylvinyl ethers, and cycloaliphatic vinyl ethers.

3. The polymerizable material of claim 1, wherein said at least one vinyl ether has a molecular weight of less than 15,000 g/mol.

4. The polymerizable material of claim 1, wherein said at least one vinyl ether is in the form of a liquid at room temperature.

5. The polymerizable material of claim 1, wherein said at least one vinyl ether includes additional functional groups.

6. The polymerizable material of claim 1, wherein said at least one vinyl ether includes difunctional vinyl ethers.

7. A method of using the polymerizable material of claim 1 as part of a dental procedure.

8. A method of using the polymerizable material of claim 1 as filling material, core build-up material, dental cement, temporary crown and bridge material, material in dental technology, or for the production of inlays, onlays, veneers and model materials.

9. A container containing component I and component II of the polymerizable material of claim 1.

10. A process of preparing dental materials comprising the polymerizable material of claim 1, said process comprising:
   initiating free-radical polymerization of vinyl ethers in the materials using an initiator system having at least one barbituric acid derivative or malonylsulfonamide,
   wherein mechanical values of the materials are increased and maximum setting temperatures are lowered.

11. A cured material formed from the polymerizable material of claim 1, wherein said cured material comprises a modulus of elasticity in bending of greater than 1500 MPa.

* * * * *

UNITED STATES PATENT AND TRADEMARK OFFICE
CERTIFICATE OF CORRECTION

PATENT NO. : 7,132,462 B2
APPLICATION NO. : 10/257011
DATED : November 7, 2006
INVENTOR(S) : Thomas Lehmann It is certified that error appears in the above-identified patent and that said Letters Patent is hereby corrected as shown below:

<u>Column 3</u>
Line 13, delete "$C_3O$-aryl" and insert -- $C_{30}$-aryl --, therefor.

<u>Column 5</u>
Line 30, delete "is-located" and insert -- is located --, therefor.

<u>Column 6</u>
Line 44, in (Table 2), delete "(ø < 12 μm)    silanized"
  and insert -- (ø < 12 μm) silanized --, therefor.
  (Consider Space)
Line 57, in (Table 2), delete "(ø < 12 μm)    silanized"
  and insert -- (ø < 12 μm) silanized --, therefor.
  (Consider Space)
Line 60, in (Table 2), delete "(KDKH" and insert -- (HDKH --, therefor.

Signed and Sealed this

Twentieth Day of May, 2008

JON W. DUDAS
*Director of the United States Patent and Trademark Office*